United States Patent
Kulcke et al.

(10) Patent No.: US 12,426,786 B2
(45) Date of Patent: Sep. 30, 2025

(54) MEDICAL IMAGING DEVICE FOR SPATIALLY RESOLVED RECORDING OF MULTISPECTRAL VIDEO DATA

(71) Applicant: KARL STORZ SE & Co. KG, Tuttlingen (DE)

(72) Inventors: Axel Kulcke, Tuttlingen (DE); Hannes Köhler, Tuttlingen (DE); Amadeus Holmer, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 9 days.

(21) Appl. No.: 17/874,588

(22) Filed: Jul. 27, 2022

(65) Prior Publication Data
US 2022/0360700 A1 Nov. 10, 2022

Related U.S. Application Data

(63) Continuation of application No. 17/194,860, filed on Mar. 8, 2021, now Pat. No. 11,405,560.

(30) Foreign Application Priority Data

Mar. 27, 2020 (EP) .................................... 20166380

(51) Int. Cl.
H04N 23/72 (2023.01)
A61B 1/00 (2006.01)
(Continued)

(52) U.S. Cl.
CPC ......... *H04N 23/72* (2023.01); *A61B 1/00193* (2013.01); *A61B 1/045* (2013.01);
(Continued)

(58) Field of Classification Search
CPC .... H04N 5/2352; H04N 5/77; H04N 9/04557; H04N 13/239; H04N 13/257;
(Continued)

(56) References Cited

U.S. PATENT DOCUMENTS 10,161,796 B1  12/2018  Cui et al.
11,405,560 B2  8/2022  Kulcke et al.
(Continued)

FOREIGN PATENT DOCUMENTS

EP       3189782 A1     7/2017
WO   WO 2017/118735    7/2017
(Continued)

OTHER PUBLICATIONS

European Search Report for European Application No. 20166380.4, mailed Sep. 17, 2020.
(Continued)

*Primary Examiner* — Richard T Torrente
(74) *Attorney, Agent, or Firm* — Jason H. Vick; Amped IP LLC

(57) ABSTRACT

A medical imaging device configured to spatially resolve recording of multispectral video data of an examination area of a patient including a light source having multiple optical emitters with different wavelengths in the visible and NIR spectral range. The light source has an emitter whose wavelength lies in the range of ±50% of its half-width around the intersection of the blue and green filter curves or the green and red filter curves, and the exposure control and the data processing means are arranged to separately detect the affected two of the red and green or the green and blue colour signals in an exposure pattern with activation of the emitter at the intersection point and to evaluate them in the multispectral analysis with mutually different wavelengths shifted by the two affected filter curves as two supporting point wavelengths.

24 Claims, 14 Drawing Sheets

(51) Int. Cl.
*A61B 1/045* (2006.01)
*A61B 1/06* (2006.01)
*A61B 5/00* (2006.01)
*A61B 5/024* (2006.01)
*A61B 5/1455* (2006.01)
*G06T 5/00* (2006.01)
*G06T 7/90* (2017.01)
*H04N 5/77* (2006.01)
*H04N 13/239* (2018.01)
*H04N 13/257* (2018.01)
*H04N 25/13* (2023.01)

(52) U.S. Cl.
CPC .......... *A61B 1/0638* (2013.01); *A61B 1/0646* (2013.01); *A61B 5/02405* (2013.01); *A61B 5/02427* (2013.01); *A61B 5/14552* (2013.01); *A61B 5/443* (2013.01); *A61B 5/4881* (2013.01); *G06T 5/00* (2013.01); *G06T 7/90* (2017.01); *H04N 5/77* (2013.01); *H04N 13/239* (2018.05); *H04N 13/257* (2018.05); *H04N 25/134* (2023.01)

(58) Field of Classification Search
CPC ... A61B 1/00193; A61B 1/045; A61B 1/0638; A61B 1/0646; A61B 5/02405; A61B 5/02427; A61B 5/14552; A61B 5/443; A61B 5/4881; A61B 1/00006; A61B 1/00186; A61B 1/05; A61B 1/0676; A61B 5/0537; A61B 5/0075; A61B 5/0077; A61B 5/0084; A61B 5/02433; A61B 5/14551; A61B 5/1459; A61B 5/4872; A61B 5/4875; A61B 5/6852; A61B 5/7425; A61B 5/743; A61B 5/745; A61B 5/0071; G06T 5/00; G06T 7/90
See application file for complete search history.

(56) References Cited

U.S. PATENT DOCUMENTS

| | | | |
|---|---|---|---|
| 2007/0201738 A1 | 8/2007 | Toda et al. | |
| 2008/0281154 A1* | 11/2008 | Gono | A61B 1/0669 600/109 |
| 2010/0073504 A1* | 3/2010 | Park | H04N 23/74 348/222.1 |
| 2011/0115882 A1* | 5/2011 | Shahinian | A61B 1/00193 348/E13.001 |
| 2014/0192190 A1* | 7/2014 | Takahashi | G06V 10/141 348/143 |
| 2015/0312455 A1 | 10/2015 | Venkataraman et al. | |
| 2016/0187199 A1 | 6/2016 | Brunk et al. | |
| 2017/0135555 A1 | 5/2017 | Yoshizaki | |
| 2018/0176488 A1 | 6/2018 | Dvir | |
| 2018/0224333 A1 | 8/2018 | Sakakibara et al. | |
| 2019/0018231 A1 | 1/2019 | Dixon | |
| 2019/0028662 A1* | 1/2019 | Kulcke | A61B 5/14552 |
| 2020/0386620 A1* | 12/2020 | Toda | G01J 3/2803 |

FOREIGN PATENT DOCUMENTS

| | | |
|---|---|---|
| WO | WO 2017/194993 | 11/2017 |
| WO | WO 2019/051591 | 3/2019 |

OTHER PUBLICATIONS

Notice of Allowance for U.S. Appl. No. 17/194,860, mailed Mar. 31, 2022.

* cited by examiner

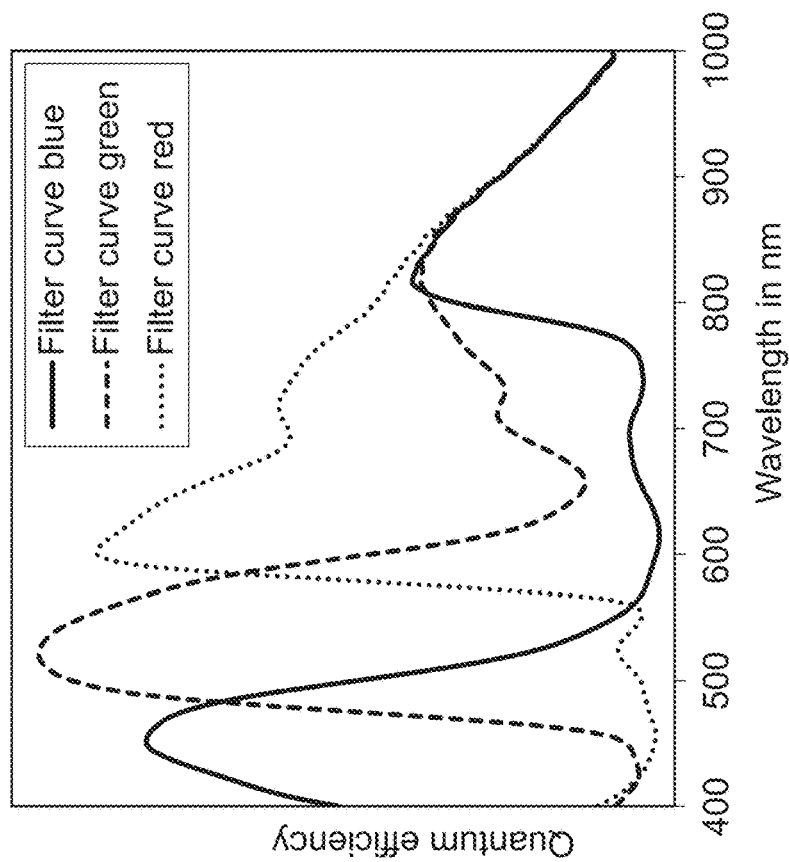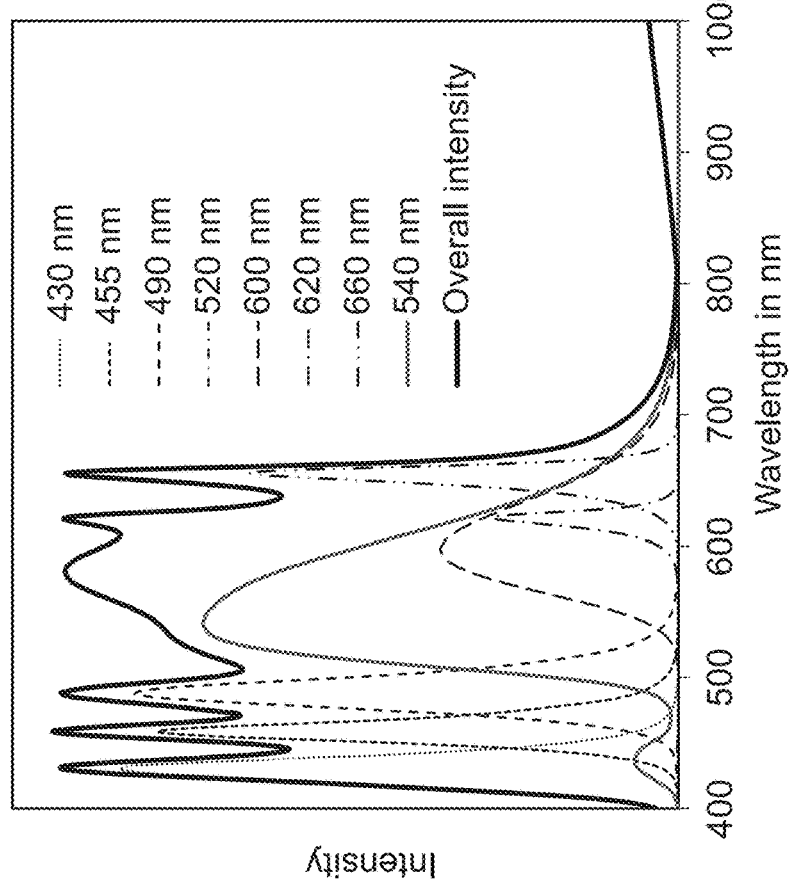
Fig. 3

MEDICAL IMAGING DEVICE FOR SPATIALLY RESOLVED RECORDING OF MULTISPECTRAL VIDEO DATA

CROSS-REFERENCE TO RELATED APPLICATIONS

This application is a Continuation of U.S. patent application Ser. No. 17/194,860, filed Mar. 8, 2021, now U.S. Pat. No. 11,405,560, which claims the benefit under 35 U.S.C. 119 (a) to European Patent Application No. 20166380.4, filed Mar. 27, 2020, all of which are incorporated herein by reference in their entirety.

SUMMARY

The present invention relates to a medical imaging device for spatially resolved recording of multispectral video data of an examination area of a patient, comprising a light source for illuminating the examination area, having a plurality of optical emitters with different wavelengths distributed over the visible and NIR spectral range, an RGB camera sensor for recording the examination area, which generates red, green and blue colour signals using filters with red, green and blue filter curves, an acquisition controller arranged for synchronized control of the light source and the RGB camera sensor to repeatedly activate one or more emitters, which together produce a spectral exposure pattern having one or more wavelengths, in a predetermined activation sequence of a plurality of successive spectral exposure patterns, each taken as an image by the RGB camera sensor, a data processing device connected to the exposure control device and the RGB camera sensor for recording the RGB camera sensor signals and for evaluating them for spatially resolved multispectral analysis to derive a physiological parameter and for spatially resolved display thereof as a video of the examination area.

The invention relates to a medical imaging device which may be integrated in an endoscope, laparoscope, microscope or exoscope. A video sequence of images is recorded using one or two (stereoscope) high-resolution colour camera sensors (RGB camera sensors) with colour filters with red, green and blue filter curves based on CMOS or CCD technology for the actual sensor.

Various optical devices are used in medicine to assist doctors in diagnosis and therapy. These devices often use high-resolution colour cameras to record the area under examination. One example is the medical video endoscope. A colour camera sensor is located at the proximal or distal exit of the endoscope. In endoscopes, the "chip in the tip" (CIT) technology is becoming increasingly popular here, in which the miniaturized colour camera sensor with imaging optics is placed directly in the tip of the endoscope (distal). The device and method described here can be used with this technology. The RGB colour camera sensors are colour filter sensors with red, green, blue colour filters arranged in a Bayer matrix. The pixels behind the red, green and blue colour filters generate red, green and blue colour signals. Illumination is provided by a light source (e.g. cold light sources with halogen lamps or xenon light sources, lasers or preferably LED light sources). The light from the light source is usually coupled into the endoscope or other optical device via fibre optics and illuminates the examination area. Such endoscopes can be designed with very high resolution (Ultra-HD) and/or three-dimensional imaging (stereoscopes).

WO 2017/118735 A2 describes a multispectral analysis method to be used on the human body, in which a light source with several LEDs of different wavelengths in the visible and in the NIR spectral range and a camera sensor are used; however, the method is not an imaging method, but serves to determine individual physiological parameters of a subject by multispectral analysis. The light source is repeatedly exposed in activation sequences with successive spectral exposure patterns when LEDs with different wavelengths are activated. However, the parameters obtained from the multispectral analysis are not displayed in a spatially resolved manner. Rather, the camera sensor is placed directly on the subject's skin and captures light transflected by the subject's tissue as a function of the distance from the light source to the capture location in order to derive physiological parameters of the subject during physical exertion, which include oxygen saturation of the arterial blood, tissue oxygen saturation, water content, pulse rate, water content of the tissue, etc.

Outside of medical image analysis, there are a number of image analysis techniques that use LEDs of different wavelengths with exposure at different wavelengths in synchronized multiplexed operation with a colour sensor to determine spectral information—see for example US 2016/0187199 A1, US10 161 796 B1 and US 2010/0073504 A1.

Classical video endoscopes are used for colour video imaging of an examination area inside the body. It is now known from physiological imaging that spectral imaging, in this case multi- or hyperspectral imaging, can provide users of endoscopes with a lot of additional information that can be used during operations or in diagnostics. A very important area in physiological imaging is perfusion imaging, which can be performed, for example, via multispectral analysis of colour signals or by fluorescence imaging.

In medical technology, physiological imaging with multispectral or hyperspectral methods is known, among other things, for the fact that physiological parameters, such as haemoglobin content and the oxygenation of haemoglobin in the examination area, which are displayed spatially resolved by false colours, contain very important clinical information for the physician. Furthermore, spatially resolved spectral imaging is also known as molecular imaging using chemometric techniques, as chemical information can be displayed spatially resolved. For clinical application, the spatially resolved representation of the haemoglobin content, especially the water content and the fat content in the tissue, are important variables.

The derivation of systemic physiological parameters such as heart rate, respiratory rate and especially the properties of the arterial blood is also of great importance and provides information with high significance about the patient's condition. There are already various approaches to combine spatially resolved imaging of a physiological parameter with the usual white light imaging (colour video).

Outside the medical field, there are a number of imaging techniques using multispectral analysis, wherein, to obtain spatially resolved multispectral information, LED light sources repeatedly illuminate an object or subject with LED emitters of different wavelengths in multiplexed operation with activation sequences of successively different spectral exposure patterns and record reflected light with a colour camera sensor, wherein the light source is timed and synchronized with the operation of the colour camera sensor such that successive exposure patterns fall into successively captured images (video frames) of the colour camera sensor.

The different spectral exposure patterns of an activation sequence can thus be captured separately and subjected to multispectral analysis.

From WO 2019/051591 A1 a medical imaging device with the features of the generic term of patent claim is known. The light source used comprises a plurality of LEDs with different wavelengths in the visible and NIR spectral range. Since an activation sequence of successive spectral exposure patterns with a corresponding number of successive images is recorded with the colour camera sensor, after the multispectral analysis the frame rate, at which the physiological information obtained from the multispectral analysis is displayed, is reduced compared to the frame rate of the colour camera sensor for a normal colour video corresponding to the number of successive exposure patterns in the activation sequence. In order to nevertheless enable a sufficient time resolution of the physiological information from the multispectral analysis, which is represented as a video in false colours, exposure patterns are used in the described method in which several LEDs are activated simultaneously at different wavelengths. The intensity information associated with the different wavelengths can be separated from each other from the three colour signals of the colour camera sensor, such techniques being referred to as spectral unmixing. This makes it possible to capture spectral information at two or more wavelengths per image captured by the colour camera sensor. In this way, activation sequences with, for example, two or three successive spectral exposure patterns, each with simultaneous activation at multiple wavelengths, may be sufficient to perform meaningful multispectral analyses with a sufficient number of spectral support points at different wavelengths.

If activation sequences are repeated, e.g. with three successive spectral exposure patterns, one after the other, and after the multispectral analysis based on this, one image of the derived physiological parameter is displayed in each case in false colours, the video of the physiological parameter, e.g. the oxygen saturation of the arterial blood, has a frame rate that is reduced to ⅓ compared to a normal colour video.

For high-quality colour video, a frame rate of 60 Hz is standard today. Accordingly, the RGB camera sensors in widespread use today are designed for such a frame rate of 60 Hz, although some camera sensors can also achieve refresh rates of up to 120 Hz. For physiological imaging of physiological parameters derived from multispectral analysis, a frame rate reduced to ⅓, i.e. typically 20 Hz, is acceptable.

It is the object of the present invention to provide a device and a method for medical imaging of a physiological parameter derived from a multispectral analysis, wherein for a given number of spectral exposure patterns per activation sequence, the largest possible number of spectral support sites (number of different wavelengths) are to be provided for the multispectral analysis.

The medical imaging device with the features of patent claim 1 and the method with the features of patent claim 14 serve to solve this problem. Advantageous embodiments are indicated in the subclaims.

The medical imaging device has a light source with an emitter, typically an LED, with a wavelength that is within ±50% of the half-width of the emitter around the intersection of the blue and green filter curves or the green and red filter curves. Wavelength here refers to the peak or peak wavelength of the emission spectrum of the emitter. The first intersection point mentioned is the intersection point of the blue filter curve sloping after its maximum with the green filter curve rising before its maximum, and the second intersection point mentioned is the intersection point of the green filter curve sloping after its maximum with the red filter curve rising before its maximum, i.e. the intersection points in the respective transition region of the said filter curves are meant. In other words, the peak wavelength of the emitter is shifted by no more than half the half-width of the emitter with respect to the wavelength of the intersection of the filter curves concerned. Said another way, the wavelength of the intersection of the affected two filter curves lies in the wavelength interval swept by the half-width of the emitter. The fact that the wavelength of the emitter is sufficiently close, namely not further than 50% of the half-width, to the intersection of the affected two filter curves ensures that both colour signals belonging to the affected filter curves account for a significant proportion of the emitter's radiated intensity.

The recording control device and the data processing device are arranged to separately record the affected two of the red and green or the green and blue colour signals in a spectral exposure pattern with activation of an emitter at one of the intersections and to evaluate them in the multispectral analysis with wavelengths shifted against each other and different from each other by the two affected filter curves two supporting point wavelengths. In this way, two colour signals with peak wavelengths shifted against each other can be recorded by an emitter due to the shift of the signals of an emitter in the two affected colour signals caused by the two affected filter curves. This makes it possible to obtain two interpolation point wavelengths for multispectral analysis by activating a single emitter.

In a preferred embodiment, the light source has a first emitter whose wavelength is within ±50% of its half-width about the intersection of the blue and green filter curves and a second emitter whose wavelength is within ±50% of its half-width about the intersection of the green and red filter curves. The exposure control and data processing means are arranged to activate the first and second emitters in different exposure patterns of the activation sequence and, when the first emitter is activated, to detect the green and red colour signals separately and to analyse them in the multispectral analysis with the blue and green filter curves shifted with respect to each other, and, when the second emitter is activated, to detect the green and red colour signals separately and to evaluate them in the multispectral analysis with wavelengths that are shifted by the green and red filter curves and different from each other as two supporting wavelengths. In this way, the first and second emitters detect a total of four different wavelengths for the multispectral analysis.

In another embodiment, the light source comprises a first emitter whose wavelength is less than ±50% of its half-width less than the wavelength at the intersection of the blue and green filter curves, and a second emitter whose wavelength is less than ±50% of its half-width greater than the wavelength at the intersection of the blue and green filter curves. The recording control and data processing device are set up to activate the first and second emitters in different exposure patterns of the activation sequence and to detect the green and blue colour signals separately both when the first emitter is activated and when the second emitter is activated, and to evaluate these in the multispectral analysis in each case with wavelengths that are shifted from one another by the blue and green filter curves, as a total of four interpolation point wavelengths.

Also in this way, four interpolation point wavelengths in the blue-green transition range can be generated for multispectral analysis.

In a preferred embodiment, when the light source is controlled with an exposure pattern with one or more emitters with wavelengths in the visible range, the exposure control and data processing devices are arranged to simultaneously activate an emitter in the NIR spectral range and to subtract that one of the blue, green and red colour signals on which the exposure with the emitters in the visible range has the least influence from the other two colour signals in order to determine the effect of the exposure in the NIR spectral range, green and red colour signals on which the exposure with the emitters in the visible range has the least effect, from the other two colour signals in order to compensate for the effect of the exposure in the NIR spectral range on the other two colour signals. The red, green and blue filter curves each have, in addition to their main filter curve in the red, green and blue spectral range respectively, a filter curve in the NIR spectral range that rises again in the same way. This has the consequence that in the case of an exposure with a wavelength in the NIR spectral range, all three colour signals have increased colour signals of approximately the same strength. The colour signal that is least affected, ideally negligibly affected, by the simultaneous exposure in the visible range can then be subtracted from the other two remaining colour signals as a correction to compensate for the contribution of the exposure in the NIR range.

In such an embodiment, the exposure control and data processing means may be arranged, when controlling the light source to produce an exposure pattern with wavelengths above 500 nm, to simultaneously activate a first emitter with a wavelength in the range of 500 to 600 nm, a second emitter having a wavelength in the range of 600 to 700 nm and an emitter having a wavelength in the NIR spectral range, and then subtracting the blue colour signal, which is at least affected by the exposures in the visible range, from the green and red colour signals to compensate for the effect of the exposure in the NIR spectral range on the green and red colour signals.

In medical operation, in addition to the pictorial representation of a physiological parameter derived from the multispectral analysis, it is important to also display the examination area in the form of a colour video parallel to the video images of the physiological parameter. For this reason, in a preferred embodiment, the acquisition control device is arranged to be switchable between a white light mode of operation and a multispectral mode of operation. In the white light mode of operation, a plurality of emitters with wavelengths distributed over the visible spectral range are continuously activated simultaneously to provide continuous illumination with a spectrum approximating white light, thereby capturing the red, green and blue colour signals from the RGB camera sensor and displaying them as colour video. In the multispectral mode of operation, the acquisition control device is arranged to select exposure patterns with activated emitters in the activation sequence which, when summed, result in an approximate white light spectrum, and to display the associated summed red, green and blue colour signals as colour video with a reduced frame rate compared to the colour video in the white light mode of operation, in parallel with the spatially resolved video of the physiological parameter derived by the multispectral analysis. In this way, exposure patterns with wavelengths in the visible range are used both to generate a colour video and to generate the video representation of the physiological parameter derived from the multi spectral analysis.

In a preferred embodiment, the recording control device and the data processing device are set up to combine the intensities $I_{\lambda 1}(t)$ determined in the course of the multispectral analysis for several wavelengths in each case over the exposure patterns of several successive activation sequences to form a time average $\overline{I_{\lambda 1}(t)}$, to form therefrom the graph of a tissue spectrum with the interpolation points of the several wavelengths $\lambda_1$ and to derive therefrom as a physiological parameter a non-pulsatile, tissue-specific parameter. For example, the oxygen saturation of the microcirculation in the tissue, the tissue haemoglobin content, the tissue water content or the tissue fat content can be determined as non-pulsatile parameters.

In a preferred embodiment, the acquisition control device and the data processing device are arranged to record the spectral intensities determined in the course of the multispectral analysis for several wavelengths $\lambda_1$ for a first activation sequence as $I_{t2}(\lambda_1)$ and to record them for a later, second activation sequence as $I_{t2}(\lambda_1)$ and to evaluate the graph $\lambda_1$ of the difference of the intensities $I_{t1}(\lambda_1)$ and $I_{t2}(\lambda_1)$ formed at the support wavelengths as a function of $\lambda_1$ in order to determine a pulsatile parameter as a physiological parameter.

The temporal distance between the first and second activation sequences can be selected so that they lie within a period of the heart pulse; e.g. a difference between an activation sequence near the high point and an activation sequence near the low point of the pulse signal can be formed and evaluated. To determine physiological parameters that change slowly relative to the pulse beat, such as the oxygen saturation of the arterial blood, differences of intensity spectra $I_{t1}(\lambda_1)$ from different periods of the pulsation signal can also be formed and evaluated across periods. Two or more differences between intensity spectra $I_{t1}(\lambda_1)$ in different successive activation sequences from one or more periods of the pulsation signal can also be formed and evaluated.

As pulsatile parameters, e.g. the oxygen saturation of the arterial blood, the heart rate, the pulsation index or the heart rate variability can be determined.

In a preferred embodiment, two RGB camera sensors are present and arranged relative to each other to enable stereoscopic images.

The data processing device is set up to evaluate the signals from the two RGB camera sensors in such a way that a stereoscopic colour video is displayed and a stereoscopic representation of the physiological parameter derived by the multispectral analysis in a spatially resolved manner is displayed.

In a preferred embodiment, the medical imaging device has an excitation light source for illuminating the examination area with excitation light in the blue or violet spectral region. The excitation light source is designed in such a way that its spectrum of excitation light is blocked by one of the red and green filter curves so that, in contrast, longer wavelength fluorescent light can be detected by the RGB camera sensor undisturbed by the excitation light.

In a preferred embodiment, the medical imaging device comprises an endoscope carrying with its distal end the light source and the RGB camera sensor, which are in data exchange communication with the acquisition control device and the data processing device via leads passing through the endoscope and emerging from its proximal end.

Finally, the invention provides a method for recording multispectral video data of an examination area of a patient, for multispectral analysis for spatially resolved derivation of a physiological parameter and for spatially resolved display thereof as a video of the examination area, in which method the examination area is illuminated with a light source, which has a plurality of optical emitters with different wavelengths distributed over the visible and NIR spectral range, the examination area is recorded with an RGB camera sensor which generates red, green and blue colour signals using filters with red, green and blue filter curves, the light source and the RGB camera sensor are operated in a synchronized controlled manner by a recording control device, to activate one or more emitters of the light source each to produce a spectral exposure pattern having one or more wavelengths, and to produce, in a predetermined activation sequence, a plurality of successive predetermined exposure patterns, the reflection of which in the examination area is respectively recorded as one image per exposure pattern by the RGB camera sensor, and the colour signals of the RGB camera sensor are subjected to a spatially resolved multispectral analysis in a data processing device which is connected to the recording control device and via the latter to the RGB camera sensor, and the colour signals of the RGB camera sensor are subjected to spatially resolved multispectral analysis in a data processing device which is connected to the recording control device and via the latter to the RGB camera sensor, in order to derive a physiological parameter, and to generate video data for spatially resolved representation of the parameter as a video of the examination area, characterized in that an emitter of the light source, whose wavelength lies in the range of ±50% of its half-value width around the wavelength of the intersection point of the blue and green filter curve or the green and red filter curve is activated in an exposure pattern, and the two colour signals concerned, which are assigned to the two filter curves of the intersection point in whose range the emitter lies, are evaluated in such an exposure pattern by the data processing device in the multispectral analysis with wavelengths which are shifted with respect to one another by the two filter curves concerned and differ from one another as two supporting point wavelengths.

By normalizing the intensity signals of the different emitters to a reference (white balance), the data points of the reflection profile and the absorption profile of the considered examination area can be calculated at each image point from the measured intensities. Thus, the methods from spectroscopy and multispectral/hyperspectral camera technology are applicable for the generation of the physiological parameter images.

Another aspect that can be used with the medical imaging device is the time-resolved evaluation of the medical signals. In this context, the technology of pulse oximetry should be particularly emphasized, in which a pulsatile evaluation of the signals can be used to record the oxygenation of the arterial blood. Such evaluations with pulsatile temporal resolution can be used to visualize the pulse and respiration-dependent physiological parameters with high spatial resolution.

The pulsation of the blood by the heartbeat and the resulting temporal change of the haemoglobin concentration at a local measuring point is the basis of pulse oximetry. Pulse oximetry conventionally evaluates the pulsatile change in the absorption of light in the tissue at 660 nm and 910 nm. The light source for illumination is preferably equipped with emitters in the form of LEDs that can be clocked quickly in time. Due to the fast clocking, the pulsating signal of the arterial blood inside the tissue can be divided into a variable and a constant part. The analysis of the variable portion with the two wavelengths mentioned, at which the intensities of the saturated and unsaturated haemoglobin behave in opposite directions, allows the oxygen saturation of the arterial blood ($SpO_2$) to be calculated.

In such an evaluation, further spectral interpolation points can also be used in addition to the two wavelengths mentioned.

BRIEF DESCRIPTION OF THE DRAWINGS

The invention is described below with reference to examples of embodiments in connection with the drawings, in which:

FIG. 3 shows in the graph on the left the emission spectra of a number of emitters in the visible range and the total spectrum resulting from this by superposition, and in the graph on the right the blue, green and red filter curves of an RGB camera sensor.

DETAILED DESCRIPTION

Figure 1:
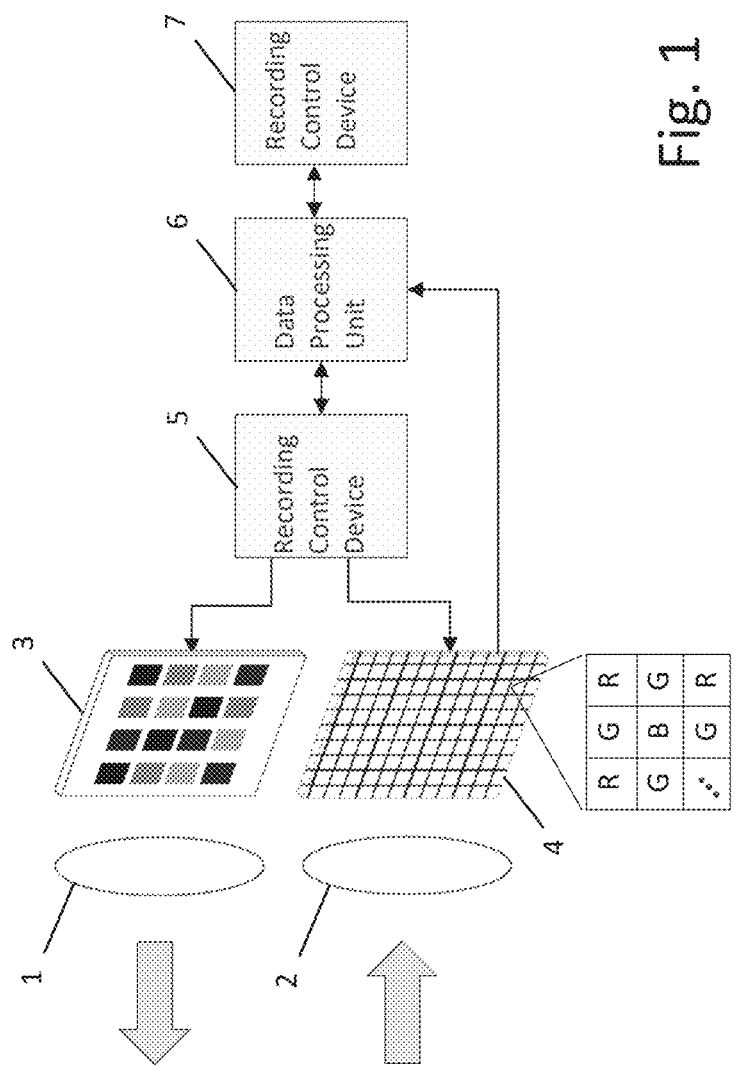
FIG. 1 schematically shows the structure of a medical imaging device according to the invention, FIG. 2 schematically shows the structure of a stereoscopic embodiment of the medical imaging device.

FIG. 1 shows a schematic block diagram of the structure of a medical imaging device which can be operated according to the present invention. The imaging device comprises a light source 3, which is shown schematically as a matrix with several emitters shown in different shades of grey. The emitters may be formed by LEDs whose wavelengths are distributed over the visible and NIR spectral ranges. Where the phrase is used herein that the emitters each have "one" wavelength, this refers to the peak wavelength of the emission spectrum of the respective emitter. Further details of the light source are described below.

The light from the light source 3 is directed onto the examination area via an imaging lens 1. The light reflected from the examination area is directed via a lens 2 onto an RGB colour camera sensor 4. The red, green and blue colour filters designated R, G and B are arranged in the so-called Bayer pattern directly in front of the pixels of the camera sensor, which may be a CMOS or CCD sensor. Each pixel therefore directly measures only one of the three colour signals, the two missing colours are usually estimated (interpolated) from the colour values of the eight neighboring pixels.

A recording control device 5 communicates with the light source 3 and the RGB colour camera sensor 4. The recording control device 5 is arranged to synchronize and control the operation of the light source 3 and the operation of the colour camera sensor 4. The recording control device 5 is also in data exchange connection with a data processing unit 6, 7, represented here by two EDP system modules 6 and 7. The first module 6 of the data processing unit receives and processes the signals from the colour camera sensor and generates successive images (video frames) therefrom. Each successive frame represents a spectral exposure pattern from an activation sequence with several successive, different spectral exposure patterns. The activation sequences are in turn repeated sequentially in time by the recording control device. Each image of the RGB colour camera sensor taken by the module 6 thus corresponds to a specific spectral exposure pattern from the activation sequence. The successive images of the spectral illumination patterns of an activation sequence are subjected to multispectral analysis in the analysis module 7 of the data processing device using predetermined algorithms in order to derive desired information and physiological parameters, as described further below. The analysis module 7 of the data processing device may also be associated with other functions such as image storage, image analysis and other functions. The analysis module 7 of the data processing device may be based on a PC, for example. The data acquisition module 6 can in principle also be implemented in this PC; as a rule, the data acquisition module 6 is implemented in a real-time processor system.

Figure 2:
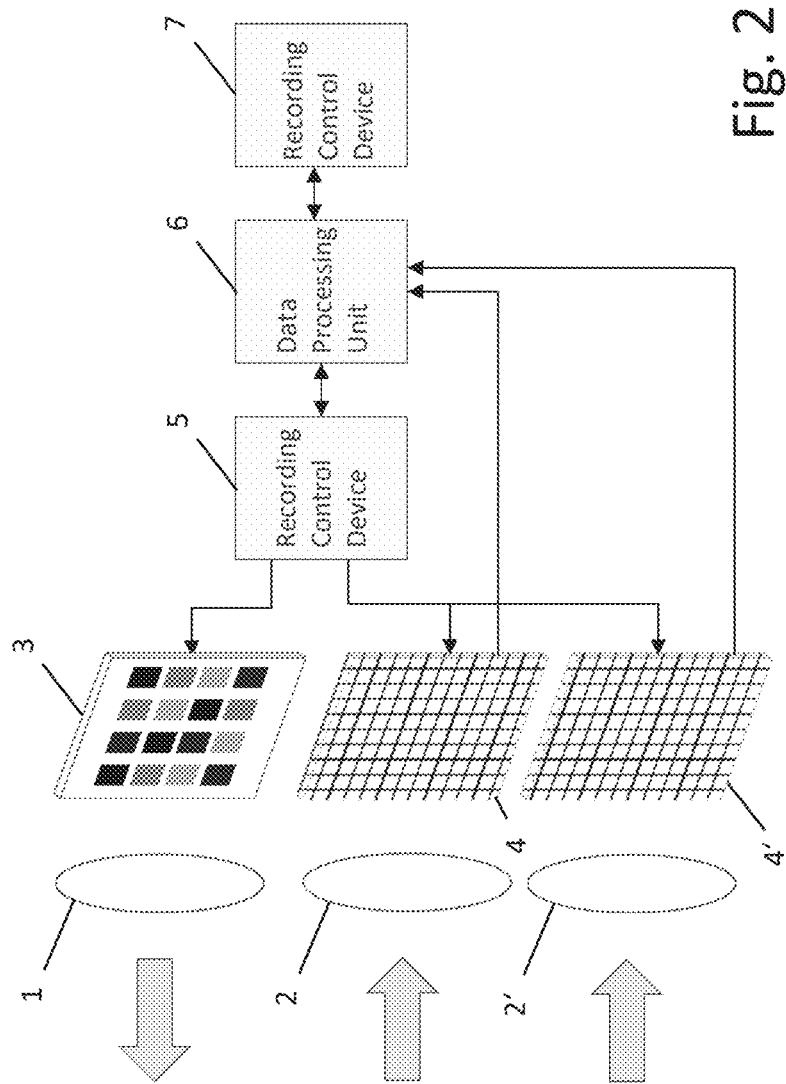

FIG. 2 shows a corresponding block diagram, whereby the medical imaging device sketched there provides stereoscopic images. For this purpose, it is provided with a further lens 2' and a further RGB colour camera sensor 4', the two lenses and the associated RGB colour camera sensors 4' being arranged in such a way that stereoscopic image information is derived from the images of the two RGB colour cameras 4, 4' in the data processing device 6, 7 in order to achieve three-dimensional imaging. In this embodiment, the RGB colour camera sensor 4 determines the synchronization as master, while the second RGB colour camera sensor 4' and the synchronized multispectral light source 3 are operated as slave.

The light source 3 comprises several LED emitters in the visible and NIR spectral range. LEDs are fast-switching, variable emitters (light pulses with a length in the range of 10 μs to 10,000 μs are typical). LEDs operate without thermal problems at high light powers that are not critical for the tissue. Preferably, the light source comprises more than 10 LEDs so that more than 10 supporting wavelengths distributed over the covered spectral range are available. In the visible spectral range, support sites should be present at local absorption maxima of oxygenated haemoglobin. This allows an additional check whether a periodic signal supposedly detected as a pulse signal is actually the pulse signal of the circulation, since the real pulse signal is accompanied by a corresponding pulse signal for oxygenated haemoglobin.

It is further preferred that the light source comprises at least one emitter with emission maximum in the range of 500 nm to 540 nm and one in the range of 570 nm to 600 nm. In particular, an emitter with a wavelength of about 520 nm and an emitter with a wavelength of 585 nm may be present. These wavelengths allow good discrimination between oxygenated and deoxygenated haemoglobin, since 520 nm is an isosbestic point of haemoglobin, i.e. the absorption coefficients of oxygenated and deoxygenated haemoglobin are equal. Another isosbestic point of haemoglobin is at 810 nm. In contrast, the absorption of deoxygenated haemoglobin at 575 nm and 880 nm is much smaller than that of oxygenated haemoglobin. At 600 nm and 760 nm, the absorption of oxygenated haemoglobin is again smaller, and therefore these four wavelengths can also be used to calculate the oxygenation of haemoglobin By using short wavelength emitters (violet), the imaging device can be used to increase the contrast between organic structures such as blood vessels, structures with different water contents or differences in concentration of other chromophores. Due to the high absorption coefficients of haemoglobin in this spectral range with constant scattering coefficients of the tissue, very sharp images are obtained, as the light penetrates and scatters little into the tissue.

Figure 10:
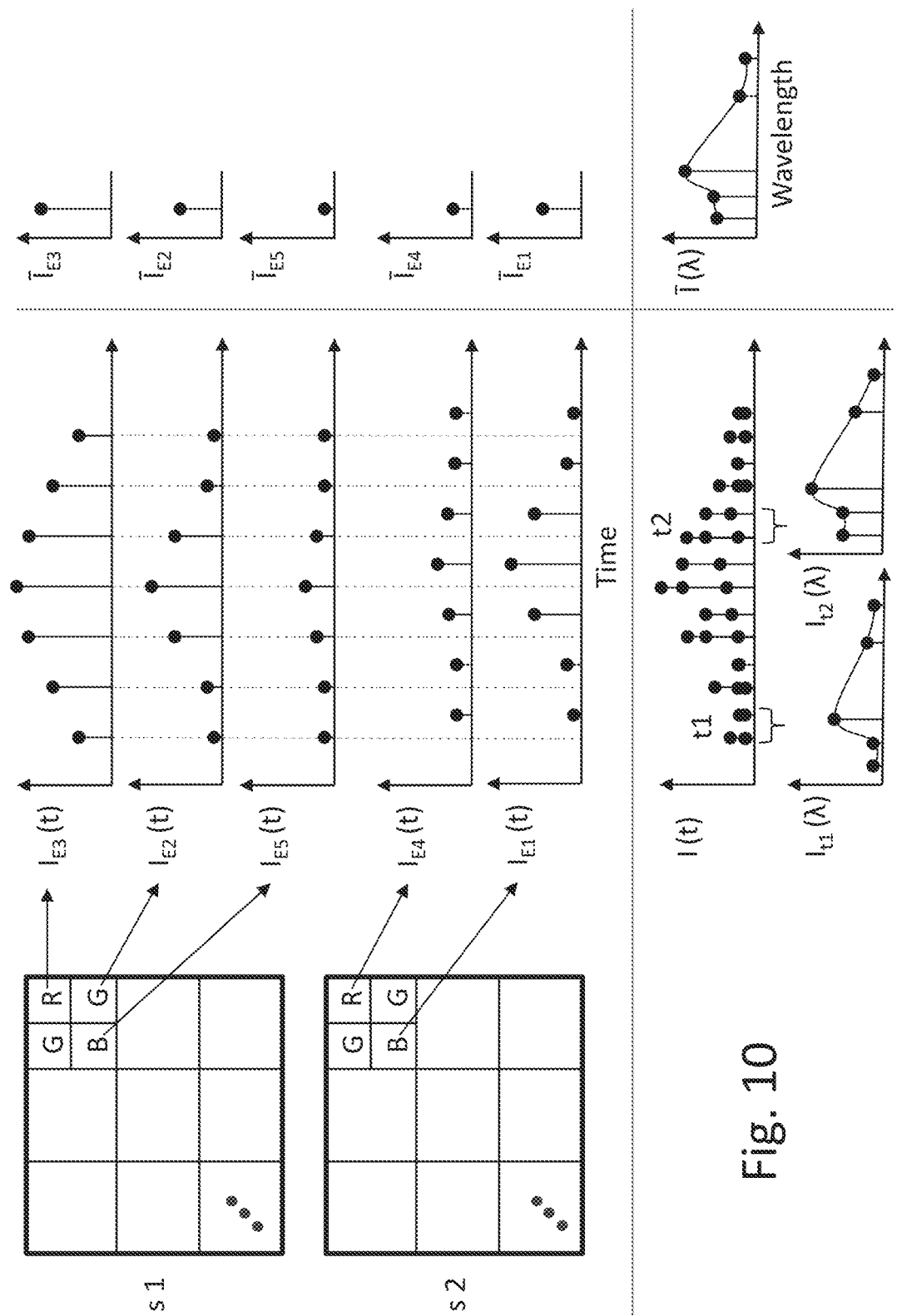
FIG. 10 shows in the middle column from top to bottom the red, green, blue colour signals and below that the red and blue colour signals for seven successive activation sequences with two successive spectral exposure patterns each according to FIG. 5 and next to it and below it summaries of the signals.

A preferred selection of wavelengths as spectral interpolation points are listed in Table 1 and shown in FIG. 10.

TABLE 1

| Preferred emission wavelengths of the light source | |
|---|---|
| Wavelength in nm | Function |
| 405 | Haemoglobin absorption for contrast enhancement Excitation of fluorescence in the red channel |
| 430 | Haemoglobin absorption for contrast enhancement Excitation of fluorescent dyes and autofluorescence in tissue |
| 455 | Colour image (blue channel) |
| 490 | Colour image (CRI) Oximetry wavelength Splitting into 2 wavelengths through colour filter of the camera sensor(Blue Green) |
| 520 | Colour image (green channel) Isosbestic point haemoglobin absorption |
| 540 | Support of colour video and additional interpolation point |
| 600 | Colour image (CRI) Oximetry wavelength Splitting into 2 wavelengths through colour filter of the camera sensor(Green Red) |
| 620 | Colour image (red channel 1) Oximetry wavelength Pulse oximetry |
| 660 | Colour image (red channel 2) Oximetry wavelength Pulse oximetry |
| 760 | Local absorption maximum of deoxygenated haemoglobin |
| 810 | Isosbestic point haemoglobin absorption |
| 880 | Pulse oximetry Reference wavelength for haemoglobin, water and fat absorption |
| 930 | Local absorption maximum of fat |
| 960 | Local absorption maximum of water |

Figure 5:
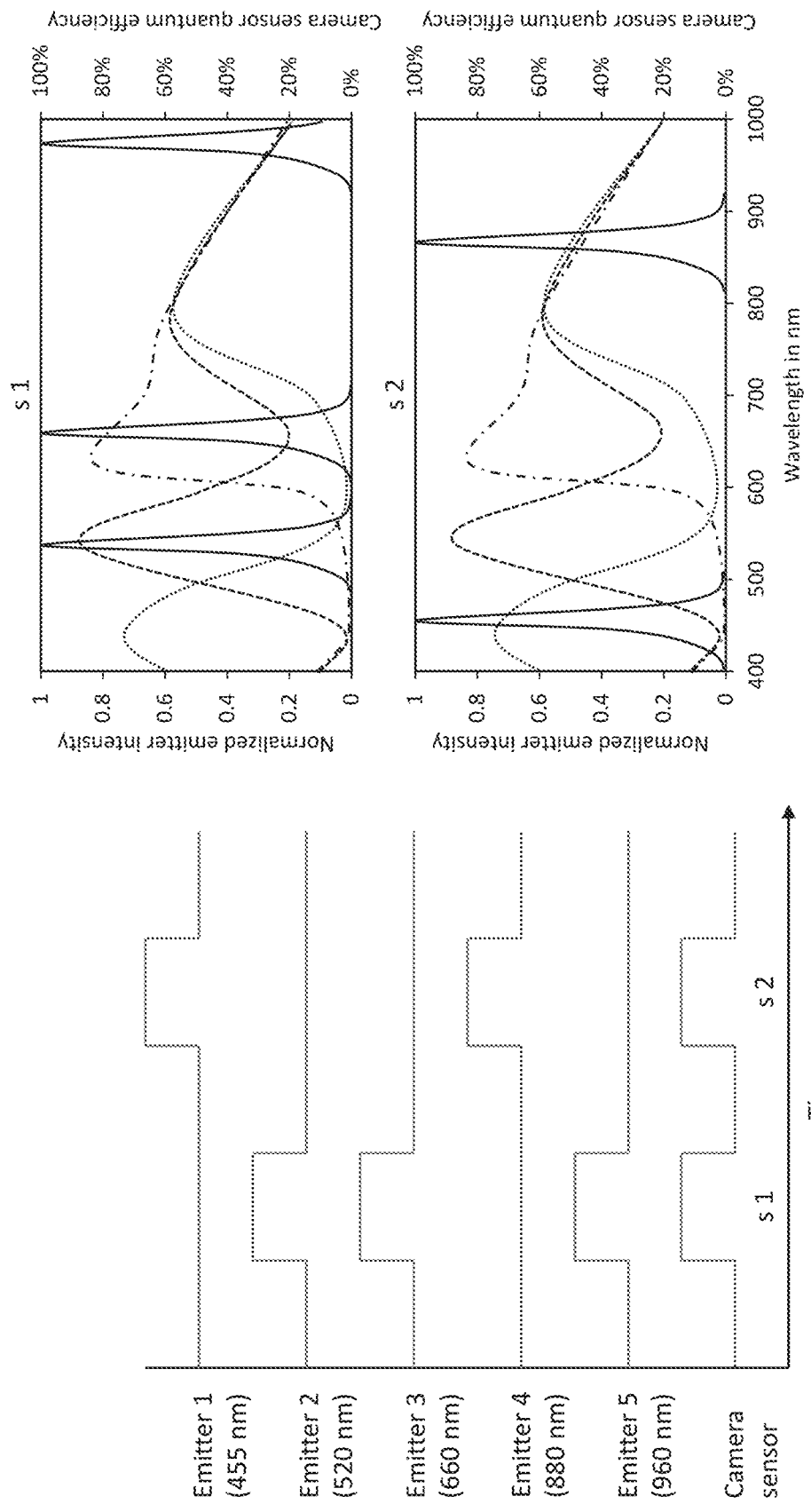
FIG. 5 shows on the left an activation sequence with two successive spectral exposure patterns, in each of which several emitters emit light pulses, and in the right part the emission spectra of the first exposure pattern (S1-top) and the second exposure pattern (S2-bottom) in each case together with the red, green and blue filter curves of the RGB camera sensor.

The recording control device is arranged, e.g. by programming, to generate a sequence of spectral exposure patterns in a predetermined activation sequence, whereby in each individual spectral exposure pattern one or more emitters with different wavelengths are activated, and to repeat this activation sequence successively in time. Each spectral exposure pattern of the activation sequence is recorded with an image of the colour camera sensor. This synchronization between the light source 3 and the colour camera sensor 4 is provided by the recording control device 5. FIG. 5 shows an example of an activation sequence not covered by the claims of the application with two successive spectral exposure patterns S1 and S2. In the graph shown on the left side of FIG. 5, the activation of five emitters during two successive spectral exposure patterns S1 and S2 as well as the recording activity of the colour camera sensor are shown as a function of time. At a maximum frame rate of the colour camera sensor of 120 Hz, two spectral exposure patterns (the first with simultaneous activation of emitters at 520, 660 and 960 nm, and the second with simultaneous activation of two emitters at 455 and 880 nm) are generated here repeatedly one after the other in an activation sequence. Thus, through efficient selection of the emitters and utilizing the three colour images of the colour camera sensor, five spectral interpolation wavelengths are available, with two images being captured by the colour camera sensor per activation sequence, so that the frame rate for multispectral imaging with five interpolation wavelengths is 60 Hz. These spectral wavelength support points can be used, for example, for simultaneous calculation of a colour video image, spatially resolved SpO$_2$ representation and spatially resolved tissue water index representation.

The number of spectral exposure patterns and the selection of emitters to be activated in the respective exposure patterns can be set during operation of the exposure control unit. control device. For this purpose, an input device can be provided in which the user enters the number of spectral exposure patterns in the activation sequence and then, for each spectral exposure pattern, the respective emitters to be activated. Thus, if required, a higher number of spectral intercept wavelengths can be recorded at a lower frame rate or, conversely, a lower number of spectral intercept wavelengths can be recorded at a higher frame rate.

The activation sequence illustrated in FIG. 5 with two successive spectral exposure patterns can be used to generate a colour image (colour video), a physiological parameter video representing the water concentration (water absorption band 960 nm to reference point 880 nm) and to generate a parameter video for SpO$_2$, the latter extracted from the pulsatile part of the signal at 660 nm, 880 nm and 960 nm. During the first spectral exposure pattern, emitter 2 (520 nm), emitter 3 (660 nm) and emitter 5 (960 nm) are switched on. The normalized intensity of the emitters and the colour filter curves of the colour camera sensor are shown in the graph at the top right. The largest signal component in the blue colour signal comes from emitter 5. Since the sensitivity of the colour camera sensor above 800 nm is almost identical in the three colour channels R, G and B, the information about the signal intensity of emitter 5 in the blue colour signal can be used to correct the signal intensities of the green and red colour signals. To obtain the actual signal of emitter 2 (520 nm), the blue colour signal is subtracted from the green colour signal. To determine the actual signal of emitter 3 (660 nm), the measured blue colour signal is subtracted from the red colour signal. Thus, after the recording of the first image (of the first spectral exposure pattern S1), there are already two supporting points in the visible and one in the near-infrared range. For the second spectral exposure pattern S2, only emitters 1 (455 nm) and 4 (880 nm) are switched on. The red colour signal comes only from emitter 4. The signal from emitter 1 can be calculated by subtracting the blue colour signal from the red colour signal. After completion of the activation sequence with the two spectral exposure patterns S1 and S2, five spectral interpolation wavelengths are available.

Figure 6:
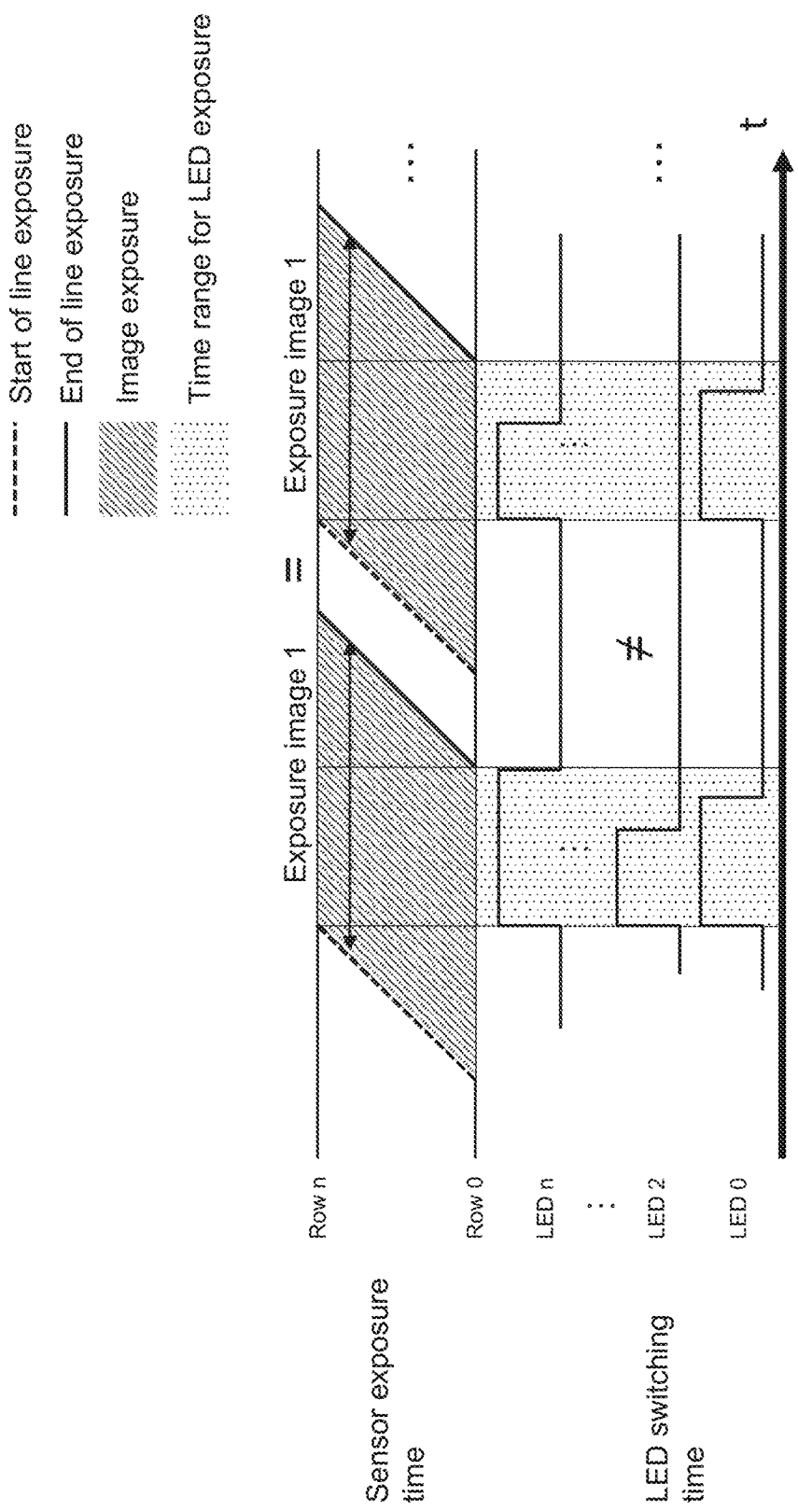
FIG. 6 shows the time sequence of exposure and readout of the RGB camera sensor with rolling shutter, FIGS. 7a-7c each show on the left the emission spectra of a spectral exposure pattern of an activation sequence with three successive spectral exposure patterns (FIGS. 7a, 7b and 7c) each together with the three colour filter curves, each show two resulting colour signals in the center and the third resulting colour signal in the right column.

FIG. 6 shows the time sequence of reading out and exposing CMOS colour camera sensors of the rolling shutter type. These CMOS colour camera sensors do not have a global shutter, so that individual lines of the camera sensor chip are read out continuously and with a time delay relative to one another, which can lead to overlapping of the exposure within individual frames when the LED emitters are activated sequentially. To solve this problem, a certain dead time is provided between successive spectral exposure patterns of the LEDs, which corresponds at least to the readout time and/or reset time of the CMOS sensor. Alternatively, it is conceivable that the exposure times of the spectral exposure patterns are selected to be greater than the time intervals between a reset and a readout of the entire CMOS sensor.

Figure 4:
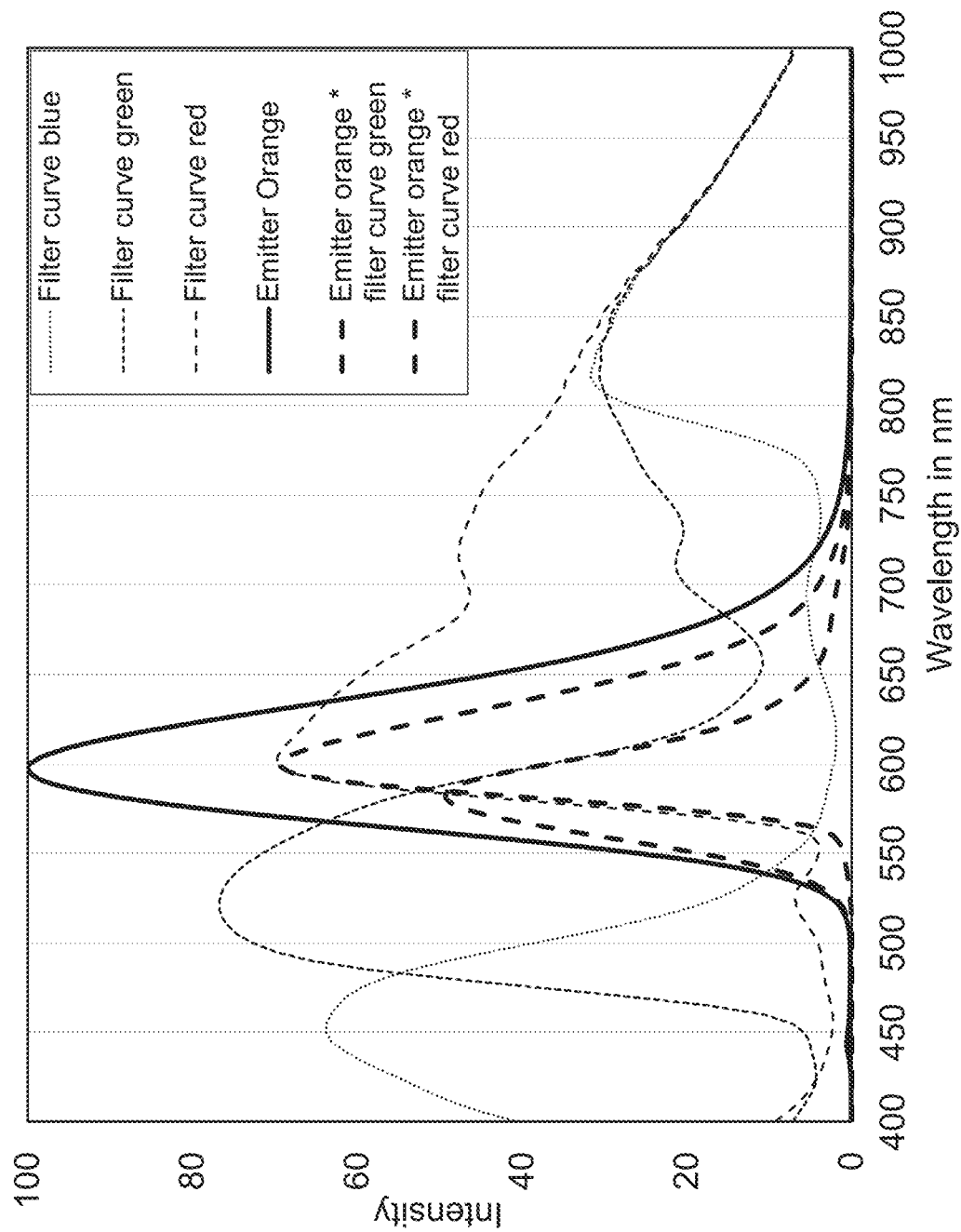
FIG. 4 shows the spectral emission curve of a broadband orange LED emitter, the three colour filter curves of the RGB camera sensor and the resulting spectral signal distribution in the green and red color signals.

FIG. 4 illustrates the generation of two spectral interpolation points from the emission curve of a single emitter (emitter orange) and the colour filter curves of the colour camera sensor. The wavelength of the orange emitter (its peak wavelength is close to the intersection of the green filter curve and the red filter curve). Due to the green and red filter curves running in opposite directions, the resulting signal maxima in the green and red colour signals are shifted in opposite directions by a few nanometers. The signal maximum in the green colour signal is shifted in relation to the maximum of the emission curve of the orange colour signal. The signal maximum in the green colour signal is shifted to smaller wavelengths compared to the maximum of the emission curve of the orange emitter, while the signal maximum in the red colour signal is shifted to longer wavelengths compared to the orange emitter. Effectively, the emission curve of the emitter is divided into two wavelength maxima in the two colour signals in the intersection area of the filter curves by the two filter curves. By decomposing the emission curve into two adjacent signal maxima in the resulting colour signals, the number of wavelengths that can be evaluated (supporting points) can be effectively increased for multispectral analysis using a single emitter.

Figure 7A:
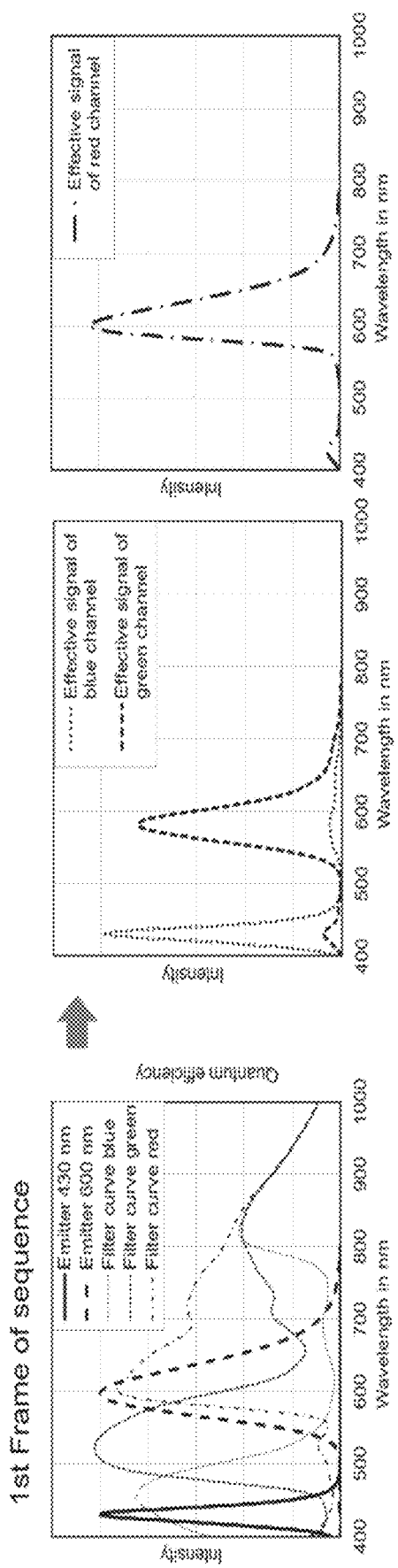
Figure 7B:
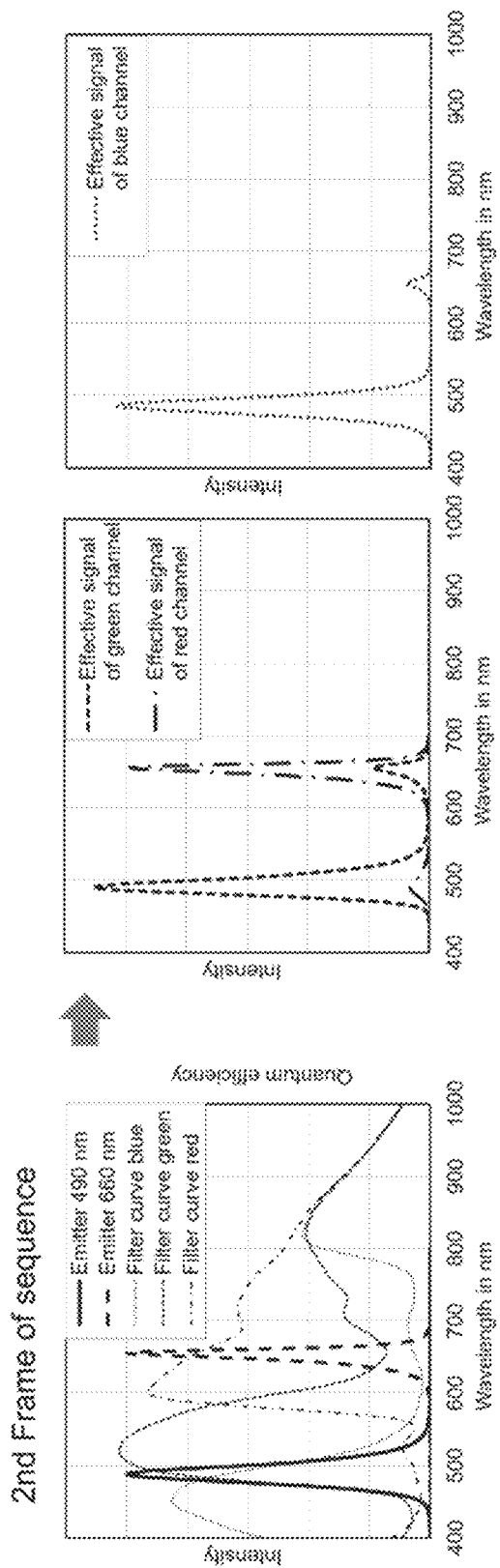
Figure 7C:
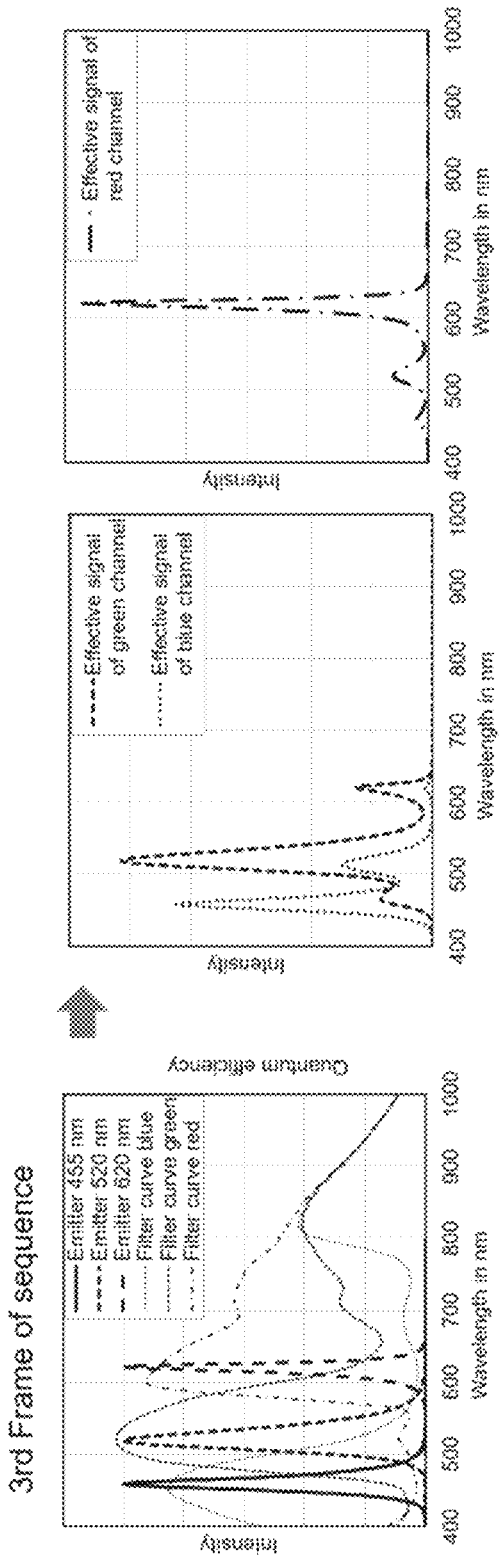
Figure 9:
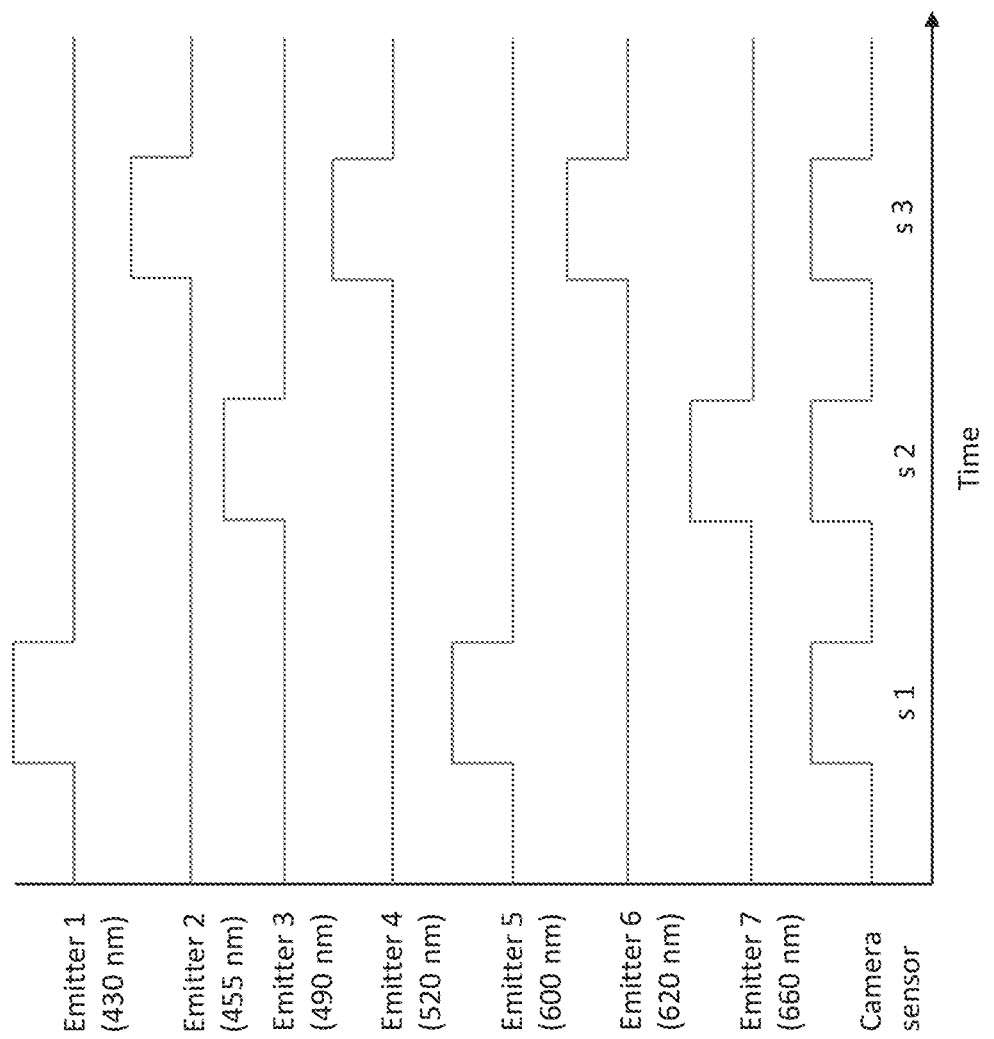
FIG. 9 shows a graph of the activation sequence with the three successive spectral exposure patterns S1, S2 and S3 as a function of time for the activation sequence shown in FIG. 7.

FIGS. 7a-7c illustrate an activation sequence that exploits the effect just described of splitting the spectrum of an emitter near the intersection of the green and red filter curves into mutually shifted green and red colour signals. Such an activation sequence is applicable in an imaging device according to the invention. The activation sequence with three successive spectral exposure patterns is shown in FIGS. 7a to 7c respectively in the form of emission spectra of the emitters involved and the resulting colour signals for the first (FIG. 7a), the second (FIG. 7b) and the third spectral exposure pattern (FIG. 7c); FIG. 9 illustrates these spectral exposure patterns in the form of a graph of the activation periods of the individual emitters and the camera sensor as a function of time over the three successive spectral exposure patterns S1, S2 and S3. In particular, FIG. 9 shows the time sequence of the switching edges during the three spectral exposure patterns with a total of seven emitters as shown in FIGS. 7a to 7c. During the time period S1 of the first spectral exposure pattern, emitter 1 (430 nm) and emitter 5 (600 nm) are switched on. During the second spectral exposure pattern (S2), emitter 3 (490 nm) and emitter 7 (660 nm) are switched on.

For the third spectral exposure pattern over time period S3, emitter 2 (455 nm), emitter 4 (520 nm) and emitter 6

(620 nm) are switched on. The camera sensor is switched on during the phases of all three spectral exposure patterns for image recording.

The activation sequence in FIGS. 7a-7c and 9 uses seven emitters in the visible range from which nine spectral interpolation points are obtained. This activation sequence can be used, for example, to generate a colour video, a parameter video for tissue oxygenation ($StO_2$) and a parameter video of the relative tissue haemoglobin concentration.

FIG. 7a to c each show in the left graph the emission spectra of the emitters used in the three successive spectral exposure patterns together with the filter curves of the colour camera sensor. The middle and right graphs in FIGS. 7a to 7c show the effective colour signals for the three colours. The first spectral exposure pattern of the activation sequence switches on two emitters at 430 nm and 600 nm, whereby the emission spectrum of the latter emitter lies close to the intersection of the green and red filter curves and its emission spectrum is therefore split into the resulting green and red colour signals, as previously described in connection with FIG. 4, so that the first spectral exposure pattern provides three spectral interpolation points.

The second spectral exposure pattern uses two emitters at 490 nm and 660 nm, whereby the signals resulting from the first emitter at 490 nm are decomposed by the blue and green filter curves into two neighboring signal maxima in the blue and green colour signals, so that the second spectral exposure pattern also provides three supporting wavelengths.

The third spectral exposure pattern of the activation sequence switches on three emitters at 455 nm, 520 nm and 620 nm, so that the third spectral exposure pattern also provides three supporting point wavelengths. Thus, the activation sequence described in connection with FIGS. 7 and 9 yields a total of nine interpolation wavelengths. At a frame rate of 120 Hz, this results in forty complete data sets per second, each with nine spectral interpolation points for the multispectral analysis.

Figure 8:
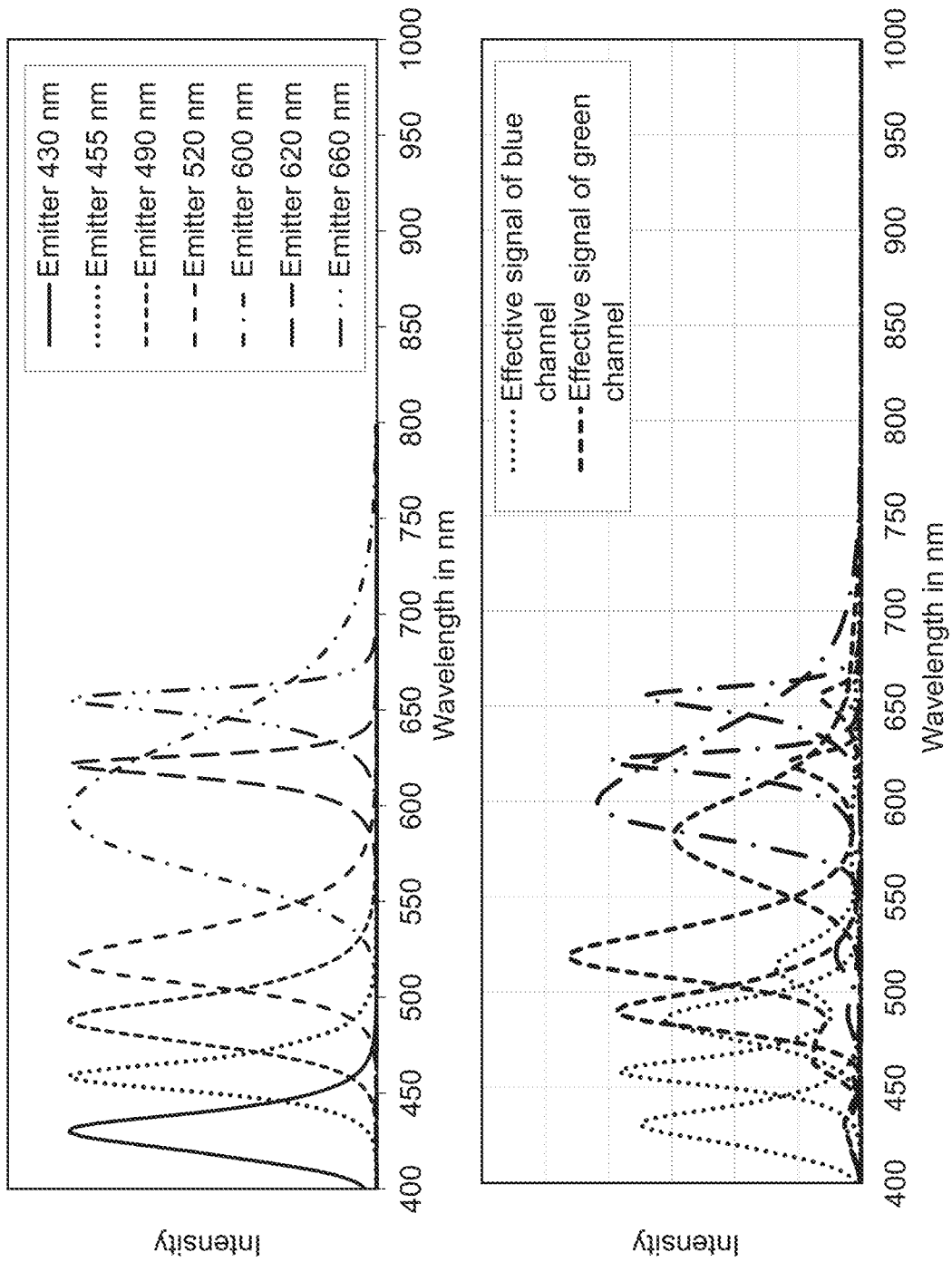
FIG. 8 shows the emission spectra of a series of LED emitters in the visible range at the top and the resulting red, green and blue colour signals at the bottom.

FIG. 8 shows in the upper graph the normalized intensities of the emitters used and in the lower graph the resulting effective three colour signals of the activation sequence described above in connection with FIGS. 7a to 7c and 9. After completion of the activation sequence of three spectral exposure patterns each, nine spectral support points are present in the visible range from 400 to 700 nm.

FIG. 10 illustrates the recording of the signals and their summary for the activation sequence of FIG. 5, which is shown repeatedly seven times in succession in the graphs in the middle column of FIG. 10. The top five in the middle column shown graphs $I_{E1}(t) \ldots I_{E5}(t)$ show the following colour signals over seven activation sequences with two spectral exposure patterns each S1 and S2: the graph $I_{E3}(t)$ shows the signal due to the emission of emitter 3 in the red colour signal (the rising and again falling course over the seven activation sequences is due to the pulsation of haemoglobin, which is clearly visible at this wavelength); the second signal sequence $I_{E2}(t)$ shows the signal resulting from the activation of emitter 2 (520 nm) in the green colour signal; the third signal $I_{E5}(t)$ shows the signal resulting from the activation of emitter 5 (960 nm) in the blue colour signal. These first three signals are each recorded simultaneously in the first spectral exposure pattern S 1 of the successive activation sequences. The fourth signal $I_{E4}(t)$ is due to the activation of emitter 4 (880 nm) and is recorded as a red colour signal. Simultaneously, the signal resulting from the activation of emitter 1 (455 nm) is recorded as a blue colour signal in the second spectral exposure pattern S2. Since the second spectral exposure pattern follows the first spectral exposure pattern of each activation sequence with a time delay, the signals $I_{E4}(t)$ and $I_{E1}(t)$ are time-delayed compared to the signals of the first spectral exposure pattern in the three upper graphs.

The right column shows the time-averaged signals (i.e. the time-averaged signals at the respective wavelengths over the seven activation phases shown in the graphs in the middle column). From these average signals at the individual wavelengths, the graph $\bar{I}(\lambda)$ with all five spectral interpolation points can be assembled (bottom right in FIG. 10), which can be evaluated as a tissue spectrum. This tissue spectrum can be used for the calculation of non-pulsatile physiological tissue parameters for which time averaging is necessary to increase the signal quality.

The graph I(t), which is shown second from the bottom in the middle column of FIG. 10, shows the measured intensities of all colour signals and the respective successive first and second spectral exposure patterns over the seven successive activation sequences of all three colour signals. Further information can be obtained from the difference of the intensities of two temporally separated activation sequences. In the two lowest graphs of the middle column of FIG. 10, the intensities $I(\lambda)$ as a function of wavelength and the intensity $I(\lambda)$ as a function of wavelength in two temporally separated activation sequences are shown. In other words, $I_{t1}(\lambda)$ shows the five spectral interpolation points recorded in the first activation sequence and the graph $I_{t2}(\lambda)$ shows the five spectral interpolation points recorded in the fifth activation sequence. The pulsatile part of the signal (time-varying part) can be derived from the difference of the interpolation points in the two graphs $I(\lambda)-I(\lambda)$. This pulsatile part can be used for the generation of the physiological parameter image for $SpO_2$, which is extracted on the pulsatile part of the signal at 660 nm, 880 nm and 960 nm.

Figure 11:
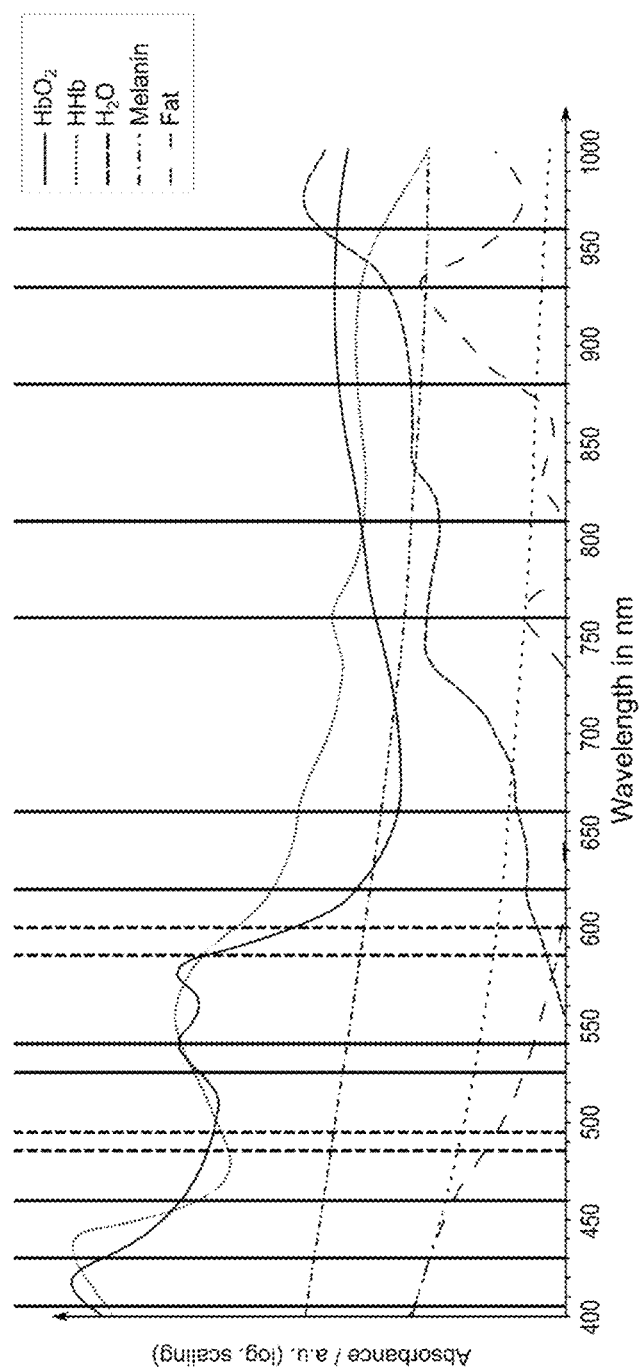
FIG. 11 shows the absorption curves of the most important absorbers of the tissue and the effective intercept wavelengths for multispectral analysis, and FIG. 12 schematically shows the composition of tissue absorption and the physiological parameters derived from it.

FIG. 11 shows the absorption curves of the main absorbers in the tissue in the visible and near-infrared range. In addition, the preferred emission wavelengths of the emitters of the light sources and the effective interpolation wavelengths resulting from this, if applicable in combination with the filter curves of the colour camera sensor, are shown.

Figure 12:
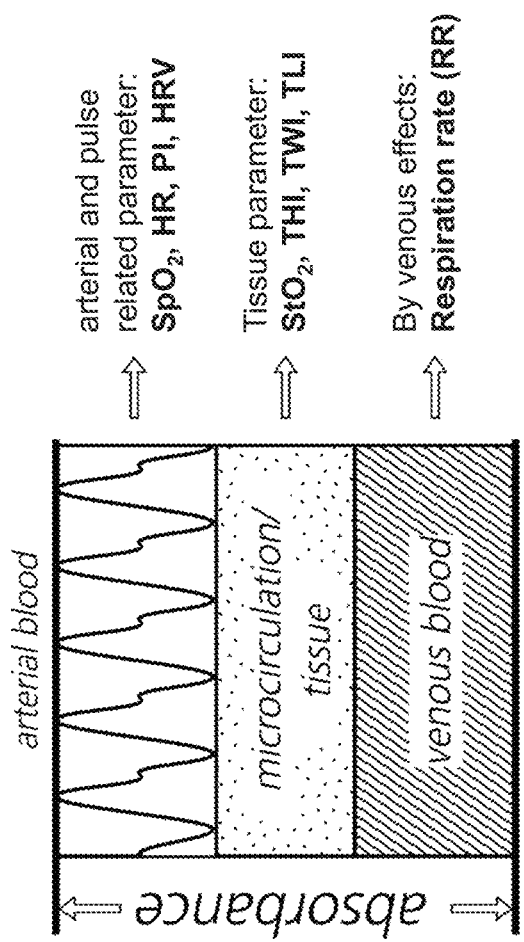

FIG. 12 shows the pulsatile and non-pulsatile signal components of tissue absorption. The pulsatile component is caused by the arterial blood and, after separation from the non-pulsatile signal component, can be used to determine the oxygen saturation of the arterial blood ($SpO_2$), the heart rate (HR), the pulsation index (PI) and the heart rate variability (HRV). The non-pulsatile signal component contains, among other things, information about the oxygen saturation of the microcirculation in the tissue ($StO_2$), the tissue haemoglobin content (THI), the tissue water content (TWI) and the tissue fat content (TLI). Another signal component is caused by the displacement of the venous blood and can be used, among other things, to determine the respiratory rate (RR).

The invention claimed is:
1. An endoscopic system comprising:
a camera sensor;
at least one lens directing light onto the camera sensor;
a plurality of LED emitters controlled by a recording control device, each of the plurality of LED emitters having an associated wavelength, one or more of the plurality of LED emitters selectively activated based on a measurement of one or more physiological parameters to be taken, wherein an activation sequence of the LED emitters, when an output of the activated LED emitters is summed, produce, in parallel, color video output and in addition to a video representation of the one or more measured physiological parameters; and
a computing device configured to receive and store one or more of images and video from the camera sensor.

2. The system of claim 1, wherein multiple combinations of the plurality of LEDs are selectively actuated in succession by the recording control device to affect a plurality of measurements.

3. The system of claim 1, wherein the measurement includes one or more of an oxygen saturation of arterial blood (SpO2), a heart rate (HR), a pulsation index (PI), and a heart rate variability (HRV).

4. The system of claim 1, wherein the measurement includes one or more of information about an oxygen saturation of a microcirculation in a tissue (StO2), a tissue hemoglobin content (THI), a tissue water content (TWI), a tissue fat content (TLI), and a respiratory rate (RR).

5. The system of claim 1, wherein one or more of pulsatile and non-pulsatile signal components are received by the computing device.

6. The system of claim 1, further comprising the computing device receiving one or more of a visible image and a video.

7. The system of claim 1, wherein through programming, the recording control device: generates a sequence of spectral exposure patterns in a predetermined activation sequence, whereby in each individual spectral exposure pattern one or more of the LED emitters with different wavelengths are activated, and repeats this activation sequence successively over time, wherein each spectral exposure pattern of the activation sequence is recorded by the camera sensor.

8. The system of claim 1, wherein synchronization between the plurality of LED emitters and the camera sensor is provided by the recording control device.

9. The system of claim 1, wherein the selective activation is caused by a user selection for a desired test.

10. The system of claim 1, wherein the associated wavelengths include one or more of 405 nm, 430 nm, 455 nm, 490 nm, 520 nm, 540 nm, 600 nm, 620 nm, 660 nm, 760 nm, 810 nm, 880 nm, 930 nm, and 960 nm.

11. A method to operate an endoscopic system comprising:
receiving, via a lens, light onto a camera sensor;
controlling, by a recording control device, a plurality of LED emitters, each of the plurality of LED emitters having an associated wavelength;
selectively activating one or more of the plurality of LED emitters based on a measurement of one or more physiological parameters to be taken, wherein an activation sequence of the LED emitters, when an output of the activated LED emitters is summed, produce, in parallel, color video output in addition to and a video representation of the one or more measured physiological parameters; and
receiving and storing one or more of images and video from the camera sensor.

12. The method of claim 11, wherein multiple combinations of the plurality of LEDs are selectively actuated in succession by the recording control device to affect a plurality of measurements for the one or more physiological parameters.

13. The method of claim 11, wherein the measurement includes one or more of an oxygen saturation of arterial blood (SpO2), a heart rate (HR), a pulsation index (PI), and a heart rate variability (HRV).

14. The method of claim 11, wherein the measurement includes one or more of information about an oxygen saturation of a microcirculation in a tissue (StO2), a tissue hemoglobin content (THI), a tissue water content (TWI), a tissue fat content (TLI), and a respiratory rate (RR).

15. The method of claim 11, wherein one or more of pulsatile and non-pulsatile signal components are received by the computing device.

16. The method of claim 11, further comprising receiving one or more of a visible image and a video at the computing device.

17. The method of claim 11, wherein through programming, the recording control device: generates a sequence of spectral exposure patterns in a predetermined activation sequence, whereby in each individual spectral exposure pattern one or more of the LED emitters with different wavelengths are activated, and repeats this activation sequence successively over time, wherein each spectral exposure pattern of the activation sequence is recorded by the camera sensor.

18. The method of claim 11, wherein synchronization between the plurality of LED emitters and the camera sensor is provided by the recording control device.

19. The method of claim 11, wherein the selective activation is caused by a user selection for a desired test.

20. The method of claim 11, wherein the associated wavelengths include one or more of 405 nm, 430 nm, 455 nm, 490 nm, 520 nm, 540 nm, 600 nm, 620 nm, 660 nm, 760 nm, 810 nm, 880 nm, 930 nm, and 960 nm.

21. An endoscopic system comprising:
a camera sensor;
at least one lens directing light onto the camera sensor;
a plurality of LED emitters controlled by a recording control device, each of the plurality of LED emitters having an associated wavelength, one or more of the plurality of LED emitters selectively activated at a specific point in time to produce light for the camera sensor, wherein the selection of the one or more of the plurality of LED emitters is based on a desired measurement of one or more physiological parameters, and a summed output of the selective activation of one or more of the plurality of LEDs are used to generate both a color video output of tissue and in addition to a physiological parameter video output representing one or more of water concentration and SpO$_2$; and
a computing device configured to receive and store one or more of images and video from the camera sensor.

22. The system of claim 21, wherein multiple combinations of the plurality of LEDs are selectively actuated in succession by the recording control device to affect a plurality of measurements for the one or more physiological parameters.

23. An system comprising:
a camera sensor at a proximal or distal end of an endoscope or exoscope;
at least one lens directing light onto the camera sensor;
a plurality of LED emitters, each of the plurality of LED emitters having an associated emissions wavelength, one or more of the plurality of LED emitters selectively activated and a corresponding output summed to produce light for the camera sensor, wherein the selection of the one or more of the plurality of LED emitters is configured to generate at the same time:
a color video output of tissue, and
a physiological parameter video output representing one or more of:
water concentration, SpO$_2$,
tissue oxygenation,
relative tissue hemoglobin concentration,
oxygen saturation of the arterial blood,
a heart rate,
a pulsation index,
a heart rate variability,
information about an oxygen saturation of a microcirculation in tissue,
tissue hemoglobin content,
tissue water content,
tissue fat content, and
respiratory rate; and a computing device configured to receive and store one or more of images and video from the camera sensor.

24. The system of claim 23, wherein the color video and the physiological parameter video are displayed simultaneously.

* * * * *

UNITED STATES PATENT AND TRADEMARK OFFICE
CERTIFICATE OF CORRECTION

Page 1 of 2

PATENT NO. : 12,426,786 B2
APPLICATION NO. : 17/874588
DATED : September 30, 2025
INVENTOR(S) : Kulcke et al.

It is certified that error appears in the above-identified patent and that said Letters Patent is hereby corrected as shown below:

In the Specification

• Column 6, Line 2, please delete "multi spectral" and insert -- multi-spectral --, therefore.

• Column 6, Line 5, please delete "$I_{\lambda 1}(t)$" and insert -- $I_{\lambda i}(t)$ --, therefore.

• Column 6, Line 8, please delete "$\overline{I_{\lambda 1}(t)}$" and insert -- $\overline{I_{\lambda i}(t)}$ --, therefore.

• Column 6, Line 10, please delete "$\lambda_1$" and insert -- $\lambda_i$ --, therefore.

• Column 6, Line 19, please delete "$\lambda_1$" and insert -- $\lambda_i$ --, therefore.

• Column 6, Line 20, please delete "$I_{t2}(\lambda_1)$" and insert -- $I_{t2}(\lambda_i)$ --, therefore.

• Column 6, Line 21, please delete "$I_{t2}(\lambda_1)$" and insert -- $I_{t2}(\lambda_i)$ --, therefore.

• Column 6, Line 22, please delete "graph $\lambda_1$ of the difference of the intensities $I_{t1}(\lambda_1)$ and $I_{t2}(\lambda_1)$" and insert -- graph $\lambda_i$ of the difference of the intensities $I_{t1}(\lambda_i)$ and $I_{t2}(\lambda_i)$ --, therefore.

• Column 6, Line 23, please delete "$\lambda_1$" and insert -- $\lambda_i$ --, therefore.

• Column 6, Line 34, please delete "$I_{t1}(\lambda_1)$" and insert -- $I_{t1}(\lambda_i)$ --, therefore.

• Column 6, Line 36, please delete "$I_{t1}(\lambda_1)$" and insert -- $I_{t1}(\lambda_i)$ --, therefore.

Signed and Sealed this
Ninth Day of December, 2025

John A. Squires
*Director of the United States Patent and Trademark Office*

CERTIFICATE OF CORRECTION (continued)
U.S. Pat. No. 12,426,786 B2

In the Claims

• Column 15, Claim 1, Line 1, please delete "andin" and insert -- in --, therefore.

• Column 15, Claim 2, Line 8, after "measurements" please insert -- for the one or more physiological parameters --, therefore.

• Column 15, Claim 11, Line 53, please delete "and", therefore.

• Column 16, Claim 21, Line 43, please delete "andin" and insert -- in --, therefore.